(12) United States Patent
Perkins

(10) Patent No.: US 8,182,533 B2
(45) Date of Patent: May 22, 2012

(54) ANNULAR REPAIR DEVICE AND METHOD

(76) Inventor: Richard Perkins, Staatsburg, NY (US)

( * ) Notice: Subject to any disclaimer, the term of this patent is extended or adjusted under 35 U.S.C. 154(b) by 573 days.

(21) Appl. No.: 12/356,017

(22) Filed: Jan. 19, 2009

(65) Prior Publication Data

US 2010/0185285 A1      Jul. 22, 2010

(51) Int. Cl.
*A61F 2/44* (2006.01)
(52) U.S. Cl. .................................................. 623/17.11
(58) Field of Classification Search .... 623/17.11–17.16; 606/280, 71–72, 281–297, 105, 68, 63
See application file for complete search history.

(56) References Cited

U.S. PATENT DOCUMENTS

| | | | |
|---|---|---|---|
| 1,118,915 A * | 12/1914 | Broluska | 403/46 |
| 2,685,877 A * | 8/1954 | Dobelle | 623/23.11 |
| 3,547,114 A * | 12/1970 | Haboush | 606/71 |
| 3,604,414 A * | 9/1971 | Borges | 606/105 |
| 4,085,744 A * | 4/1978 | Lewis et al. | 623/17.11 |
| 4,237,875 A * | 12/1980 | Termanini | 606/63 |
| 5,129,903 A * | 7/1992 | Luhr et al. | 606/71 |
| 5,405,391 A * | 4/1995 | Hednerson et al. | 623/17.15 |
| 5,800,547 A * | 9/1998 | Schafer et al. | 623/17.16 |
| 5,827,286 A * | 10/1998 | Incavo et al. | 606/71 |
| 5,941,881 A * | 8/1999 | Barnes | 606/71 |
| 5,964,762 A * | 10/1999 | Biedermann et al. | 606/71 |
| 5,980,522 A * | 11/1999 | Koros et al. | 623/17.11 |
| 6,039,762 A * | 3/2000 | McKay | 623/17.11 |
| 6,102,950 A * | 8/2000 | Vaccaro | 623/17.16 |
| 6,106,527 A * | 8/2000 | Wu et al. | 606/250 |
| 6,113,638 A * | 9/2000 | Williams et al. | 128/898 |
| 6,176,882 B1 * | 1/2001 | Biedermann et al. | 623/17.15 |
| 6,179,873 B1 * | 1/2001 | Zientek | 623/17.11 |
| 6,183,476 B1 * | 2/2001 | Gerhardt et al. | 606/71 |
| 6,200,348 B1 * | 3/2001 | Biedermann et al. | 623/17.11 |
| 6,447,546 B1 * | 9/2002 | Bramlet et al. | 623/17.16 |
| 6,471,706 B1 * | 10/2002 | Schumacher et al. | 606/70 |
| 6,527,803 B1 * | 3/2003 | Crozet et al. | 623/17.11 |
| 6,616,668 B2 * | 9/2003 | Altarac et al. | 606/252 |
| 6,699,249 B2 * | 3/2004 | Schlapfer et al. | 606/71 |
| 6,932,820 B2 * | 8/2005 | Osman | 606/71 |
| 7,124,761 B2 * | 10/2006 | Lambrecht et al. | 128/898 |
| 7,201,751 B2 * | 4/2007 | Zucherman et al. | 606/249 |
| 7,223,227 B2 * | 5/2007 | Pflueger | 600/12 |
| 7,547,305 B2 * | 6/2009 | Rapp | 606/70 |
| 7,717,961 B2 * | 5/2010 | Lambrecht et al. | 623/17.16 |
| 7,780,710 B2 * | 8/2010 | Orbay et al. | 606/286 |
| 7,935,147 B2 * | 5/2011 | Wales | 623/17.16 |
| 7,951,201 B2 * | 5/2011 | Cauthen et al. | 623/17.11 |
| 7,959,653 B2 * | 6/2011 | Thramann et al. | 606/250 |
| 7,993,374 B2 * | 8/2011 | Zucherman et al. | 606/249 |
| 8,007,521 B2 * | 8/2011 | Malandain et al. | 606/279 |
| 8,007,537 B2 * | 8/2011 | Zucherman et al. | 623/17.16 |
| 2002/0055741 A1 * | 5/2002 | Schlapfer et al. | 606/71 |
| 2003/0014117 A1 * | 1/2003 | Lambrecht et al. | 623/17.16 |
| 2003/0040796 A1 * | 2/2003 | Ferree | 623/17.11 |
| 2003/0045937 A1 * | 3/2003 | Ginn | 623/17.11 |
| 2003/0149484 A1 * | 8/2003 | Michelson | 623/17.16 |
| 2003/0153976 A1 * | 8/2003 | Cauthen et al. | 623/17.16 |
| 2003/0195514 A1 * | 10/2003 | Trieu et al. | 606/61 |

(Continued)

*Primary Examiner* — Eduardo C Robert
*Assistant Examiner* — Mary Hoffman

(57) ABSTRACT

Provided is a device and method for repairing a damaged intervertebral disc in the spine of a patient. The device provided having at two slidably engaged components that permit ease of insertion into the void created in the annulus fibrosis of the damaged disc. Also provided is a method of implanting the device into the annulus fibrosis of a damaged disc.

6 Claims, 11 Drawing Sheets

U.S. PATENT DOCUMENTS

| | | | |
|---|---|---|---|
| 2004/0002764 A1* | 1/2004 | Gainor et al. | 623/17.16 |
| 2004/0010312 A1* | 1/2004 | Enayati | 623/17.11 |
| 2004/0019353 A1* | 1/2004 | Freid et al. | 606/69 |
| 2004/0019381 A1* | 1/2004 | Pflueger | 623/17.11 |
| 2004/0102778 A1* | 5/2004 | Huebner et al. | 606/71 |
| 2004/0167521 A1* | 8/2004 | De Windt | 606/69 |
| 2004/0181226 A1* | 9/2004 | Michelson | 606/61 |
| 2005/0143825 A1* | 6/2005 | Enayati | 623/17.16 |
| 2006/0095136 A1* | 5/2006 | McLuen | 623/23.47 |
| 2006/0161162 A1* | 7/2006 | Lambrecht et al. | 606/79 |
| 2006/0195193 A1* | 8/2006 | Bloemer et al. | 623/17.16 |
| 2006/0217811 A1* | 9/2006 | Lambrecht et al. | 623/17.16 |
| 2006/0241621 A1* | 10/2006 | Moskowitz et al. | 606/72 |
| 2006/0247785 A1* | 11/2006 | Gorensek et al. | 623/17.16 |
| 2006/0271052 A1* | 11/2006 | Stern | 606/69 |
| 2007/0055375 A1* | 3/2007 | Ferree | 623/17.11 |
| 2007/0162135 A1* | 7/2007 | Segal et al. | 623/17.11 |
| 2007/0233262 A1* | 10/2007 | Arnin et al. | 623/17.15 |
| 2010/0198221 A1* | 8/2010 | Hearn | 606/71 |
| 2011/0098751 A1* | 4/2011 | Ani et al. | 606/282 |

* cited by examiner

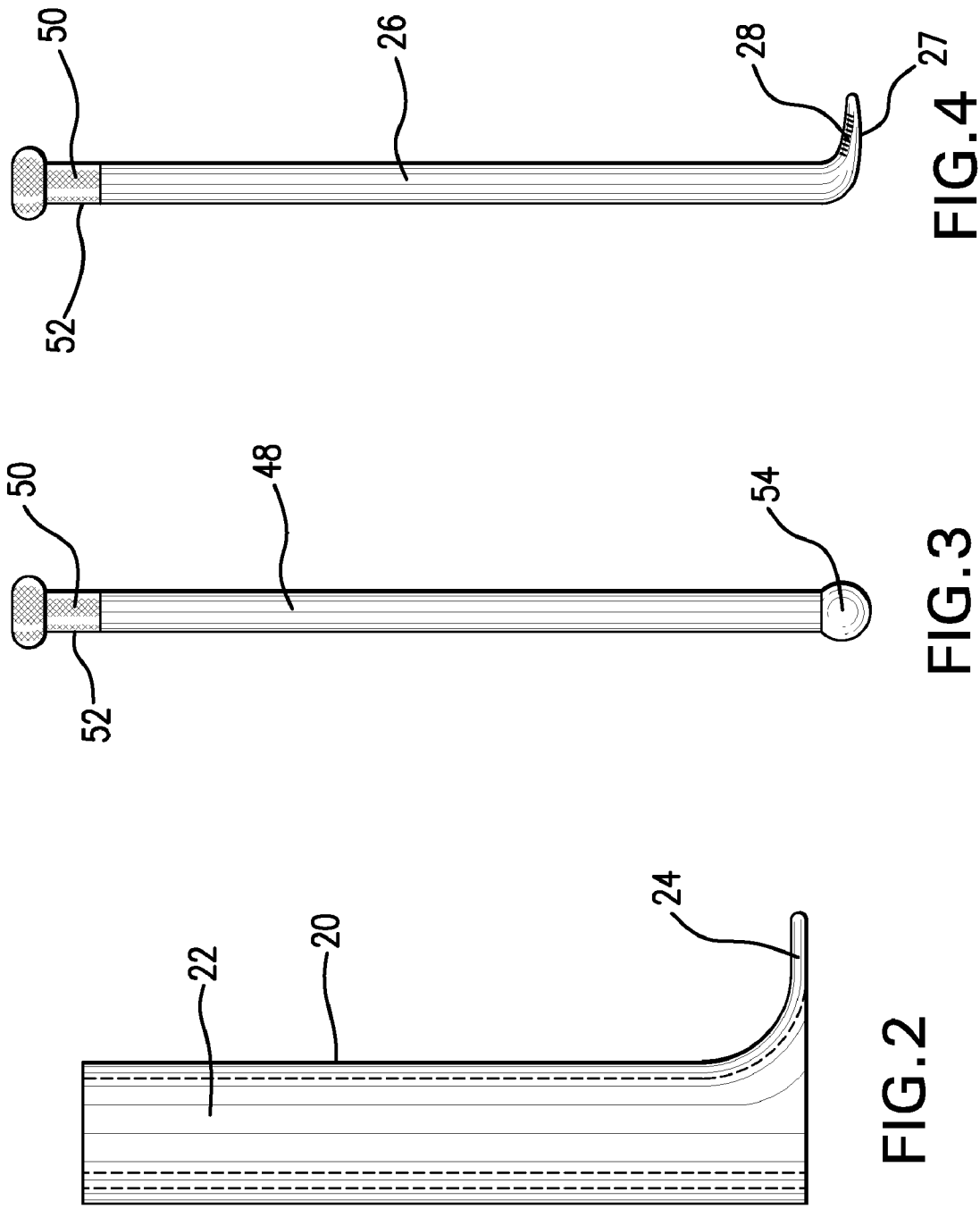

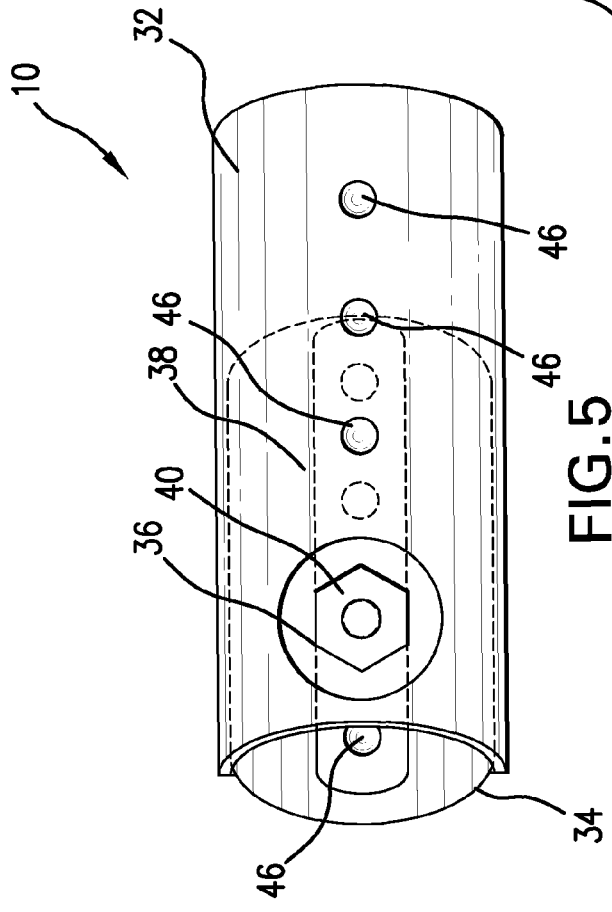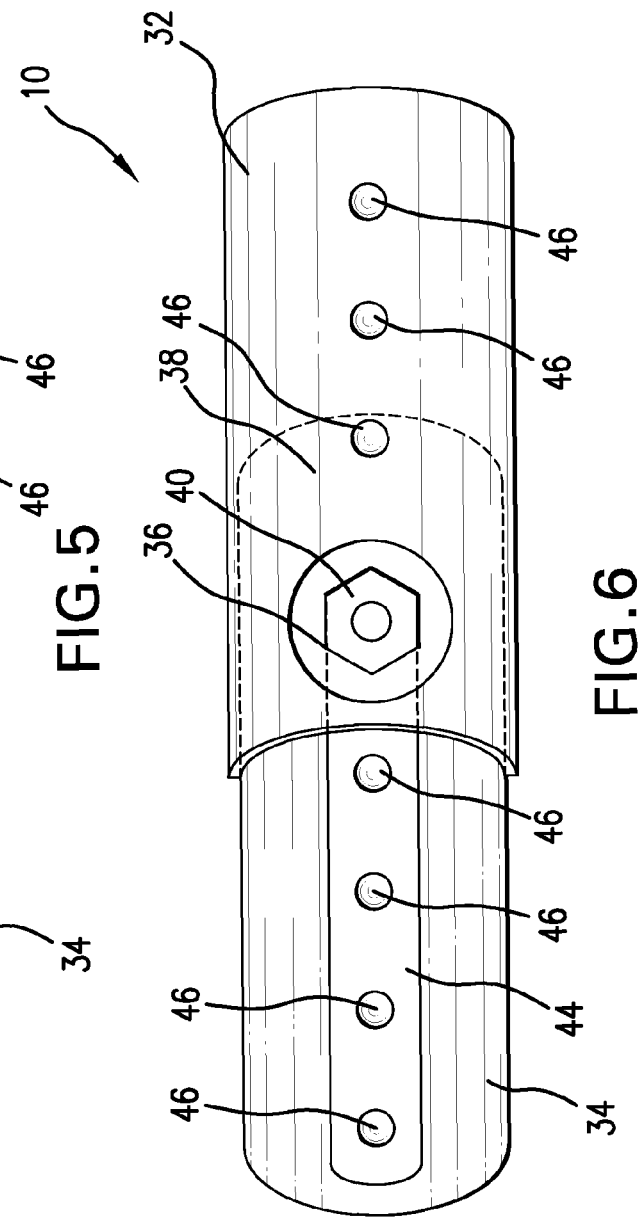

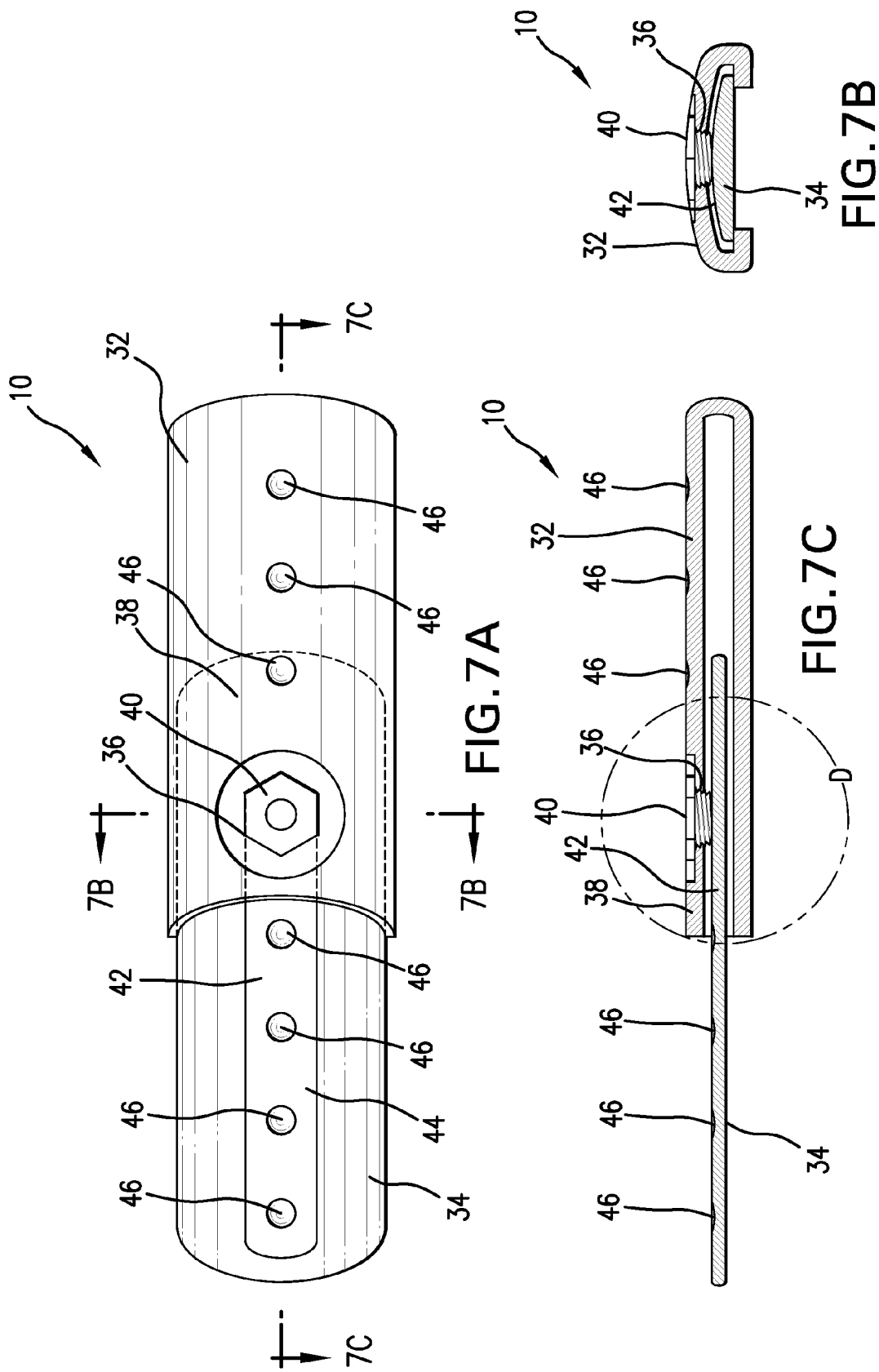

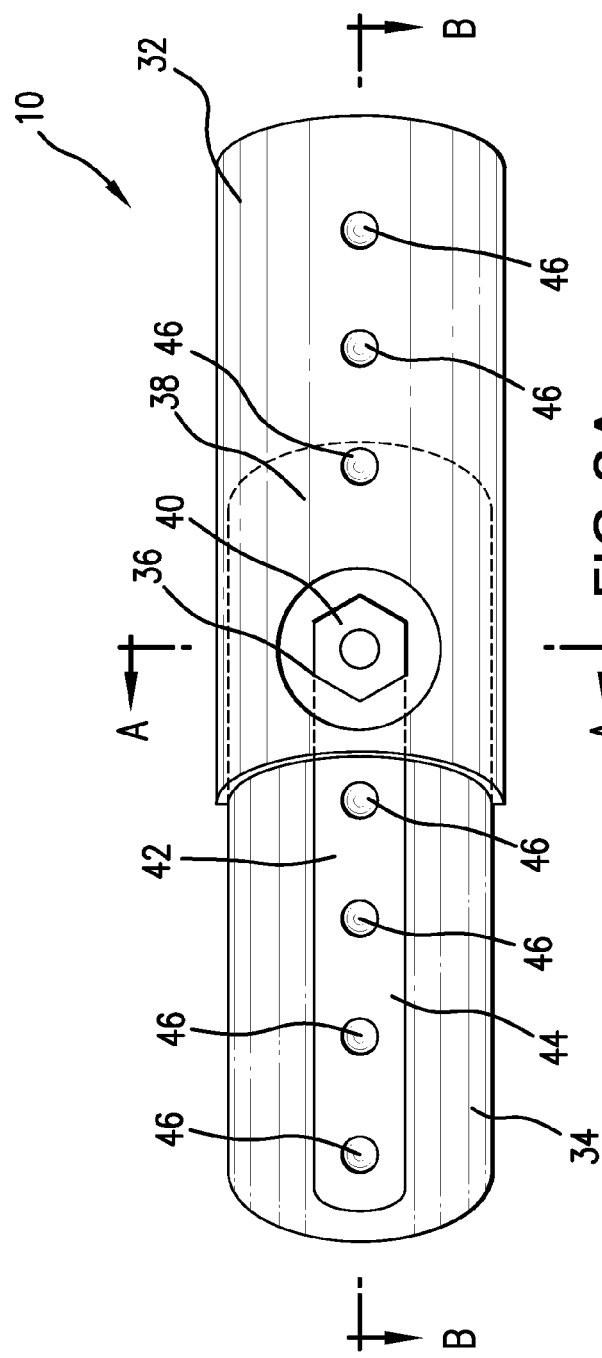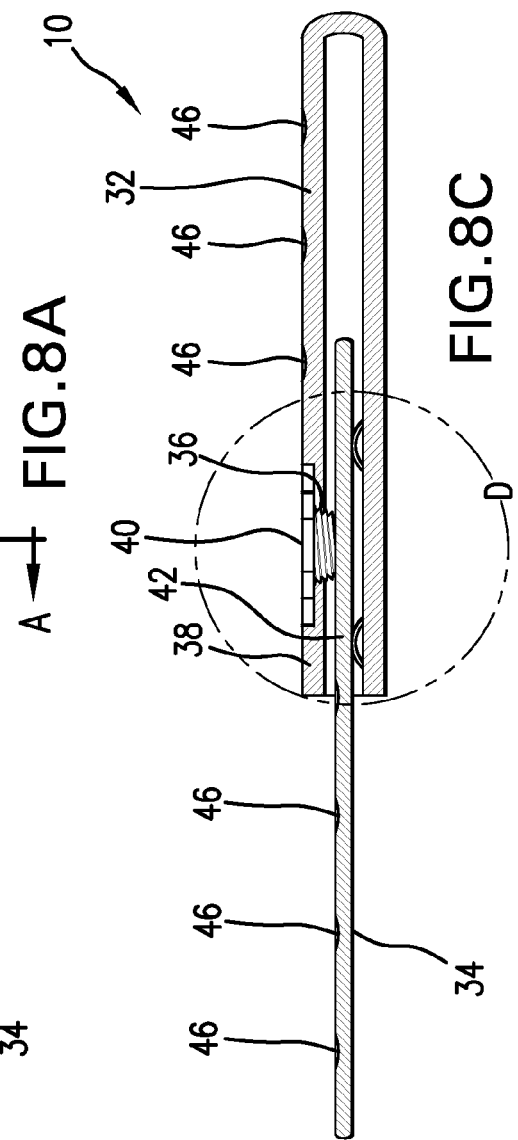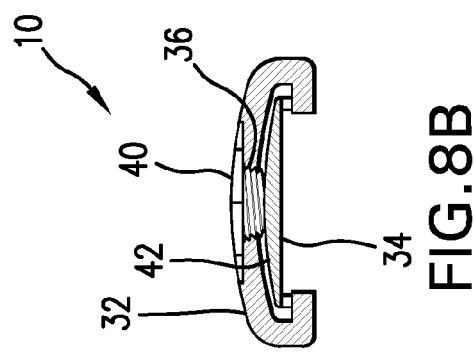

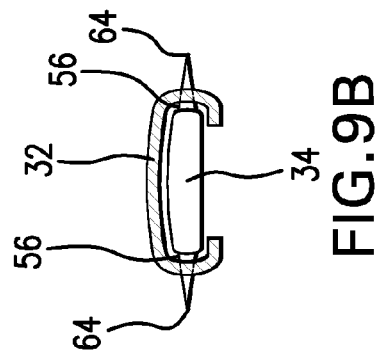
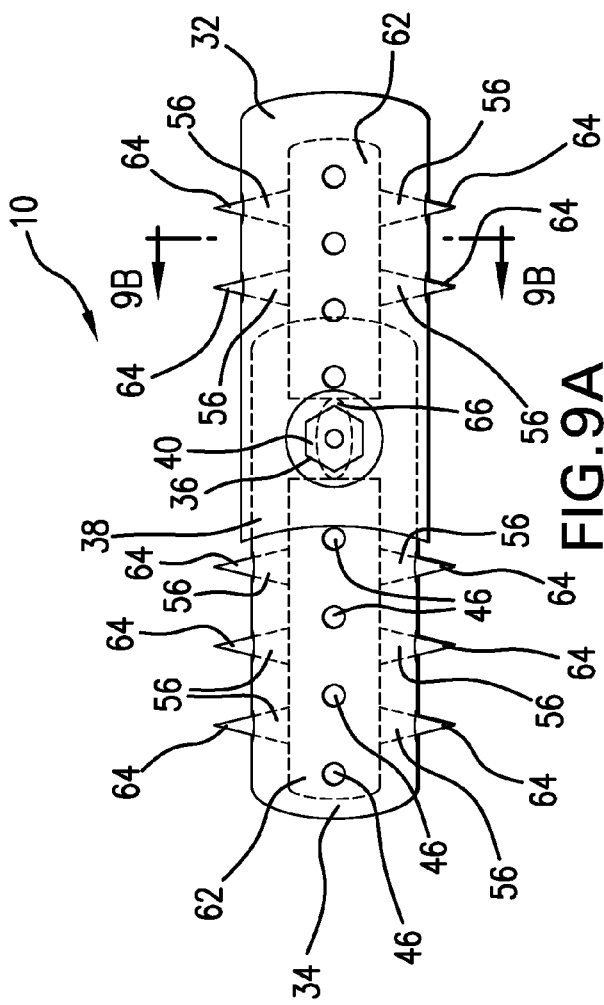
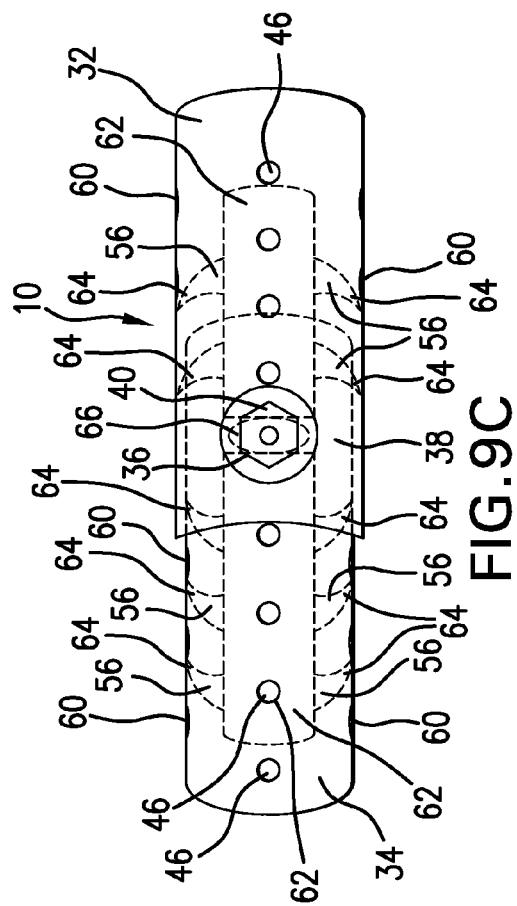

ANNULAR REPAIR DEVICE AND METHOD

BACKGROUND

1. Technical Field

The present invention relates to devices and methods for use in spine surgery. In particular, the present invention relates to prosthetic devices that can implanted in the annulus fibrosis of a intervertebral disc for purpose of occluding defects in the annulus fibrosis so as to impede further loss of nucleus pulposus through such defects. The present invention also relates to instrumentation associated with implanting such annular repair devices.

2. Background Art

The human spine is comprised of thirty-three vertebrae at birth and twenty-four as a mature adult. Between each pair of vertebrae is an intervertebral disc, which maintains the space between adjacent vertebrae and acts as a cushion under compressive, bending and rotational loads and motions. The intervertebral disc contains three major components: a nucleus pulposus (a fluid-like component comprising proteoglycans and collagen), an annulus fibrosis (a flexible, collagen-based ring surrounding the nucleus pulposus) and a pair of cartilaginous endplates which help enclose the nucleus pulposus within the annulus fibrosis. A normal, healthy nucleus pulposus acts much like a pressurized fluid by transferring and distributing compressive load to the annulus fibrosis, thereby causing a slight expansion of the annulus fibrosis. However, injury and/or degeneration of the intervertebral disc in the human spine can be caused by disc herniation, rupture of the annulus, prolapse of the nucleus pulposus, mechanical instability of the disc and/or dehydration of the disc, thereby leading to neck and back pain, pain in the extremities, numbness and weakness. In addition, damage or degeneration of the annulus fibrosis in the form of a herniation, tear and/or crack reduces its ability to resist the tensile stresses conferred by the nucleus pulposus. Thus, the disc experiences excessive bulging that may result in spinal cord and/or nerve root impingement and subsequent pain, numbness, and weakness. Further, the nucleus pulposus can herniate into the foramenal spaces, causing irritation of nerve roots and foramenal stenosis.

Treatments such as discectomy, laminectomy, laminotomy and/or spine fusion procedures represent state of the art surgical treatment for disc problems. Typically, the goal of these treatments is to relieve pressure on the neural elements by eliminating the material causing stenosis or irritation of the neural elements. However, discectomy when performed alone can result in significant loss of disc height and frequently provides only temporary pain relief. Laminectomy/laminotomy procedures also provide only temporary relief by opening up the spinal canal and decompressing the neural elements, which is susceptible to restenosis due to scar tissue formation at the operative site. Spine fusion is considered by some to be a last resort, "most" invasive procedure that eliminates the flexibility of the motion segment and usually involves permanent hardware implantation. Furthermore, fusing spinal segments has been linked to adjacent level disc degeneration. All of these techniques have the disadvantage that they require extremely invasive surgical intervention to carry out the treatment.

There is, therefore, a need for a device and an improved method for excising and repairing disc herneations in a simple less invasive manner that can seal the annulus fibrosis and prevent subsequent expulsion of nucleus pulposus from the repaired disc.

SUMMARY OF THE DISCLOSURE

The present invention meets the above identified need by providing a novel device and a minimally invasive method of implanting the device in a damaged intervertebral disc so as to repair the damaged portion of the disc and occlude any subsequent leakage of nucleus pulposus from the repaired disc.

It is an object of the invention to provide an adjustable length device having a size and configuration that can be inserted into a damaged disc without causing any additional damage to the disc or loss of nucleus pulposus.

It is also an object of the invention to provide a device for insertion into the site of disc annulus damage that can be expanded within the annulus fibrosis or within the nucleus pulposus at a position adjacent to the inner surface of the annulus fibrosis and effectively seal the damaged site so as to avoid subsequent loss of nucleus pulposus.

It is also an object of the invention to provide a device that can be anchored into position within the tissue of the annulus fibrosis or within the nucleus pulposus at a position adjacent to the inner surface of the annulus fibrosis such that no portion of the device or any attachments thereto protrude outside of the disc annulus.

It is also an object of the invention to provide a device for insertion into the site of disc annulus damage that can be selectively expanded to fill the damaged opening in the disc annulus, anchored in place in the disc without any foreign protrusions outside of the disc annulus, and be capable of subsequently having the anchors in the disc selectively released, and the length of the device subsequently shortened by the user if necessary for easy removal from the disc.

It is further an object of the invention to provide surgical instruments and tools for the insertion, adjustment, and anchoring of the device in an injured area of a disc.

It is further an object of the invention to provide a method of implanting a device in an injured area of a disc by minimally invasive surgical techniques such that no portion of the device so implanted protrudes outside of the disc annulus.

It is further an object of the invention to provide a method of implanting a device in an injured area of a disc by minimally invasive surgical techniques, adjusting the length of the implanted device so as to occlude the subsequent loss of nucleus pulposus, and anchor the device in place without any portion of the device or any attachments to the device protruding outside the disc annulus.

It is further an object of the invention to provide a kit including at least one implantable device sized and configured for insertion into a disc having damage to the disc annulus and providing at least one surgical instrument or tool for implanting the device.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 2 shows an illustration of a trocar having at least one lumen and an extended foot that can be used to facilitate insertion of the device of the present invention into a damaged disc annulus.

FIG. 3 shows an illustration of a length adjustment tool configured to facilitate adjustment of the length of the device of the present invention.

FIG. 4 shows an illustration of a device insertion site preparation tool having a distal end with a taper to a point for facilitating preparation of the annulus fibrosis to receive the device of the present invention. The site preparation tool can be provided with indicia showing the depth of insertion into the annulus fibrosis of the disc.

FIG. 5 shows an illustration of an embodiment of the device of the present invention in a collapsed configuration to facilitate ease of insertion into the damaged annulus fibrosis site of a herniated intervertebral disc.

FIG. 6 shows an illustration of the embodiment of the device shown in FIG. 5 with the device in an expanded configuration.

FIGS. 7A-D show an illustration in FIG. 7A of top view, in FIG. 7B a sectional end view, in FIG. 7C a sectional side view, and in FIG. 7D an enlarged sectional portion "D" as shown in FIG. 7C, of the device of the present invention wherein the device is provided with surface depressions that can be used to facilitate adjustment of the length of the device, a locking element that can be used to secure the two slidably interconnected portions in a selected configuration relative one to the other, and a length adjustment guide slot.

FIGS. 8A-D show an illustration in FIG. 8A of top view, in FIG. 8B a sectional end view, in FIG. 8C a sectional side view, and in FIG. 8D an enlarged sectional portion "D" as shown in FIG. 8C, of the device of the present invention, wherein the device is provided with surface depressions that can be used to facilitate adjustment of the length of the device, a locking element that can be used to secure the two slidably interconnected portions in a selected configuration relative one to the other, at least one biasing element for exerting a bias of the two interconnected portions relative one to the other, and a length adjustment guide slot.

FIGS. 9A-C show an illustration in FIG. 9A of a top view with anchoring elements extended, in FIG. 9B a sectional side view with anchoring elements extended, and in FIG. 9C a top view with anchoring elements retracted.

DETAILED DESCRIPTION OF PREFERRED EMBODIMENTS

Detailed embodiments of the present invention are disclosed herein; however, it is understood that the following description and each of the accompanying figures are provided as being exemplary of the invention, which may be embodied in various forms without departing from the scope of the claimed invention. Thus, the specific structural and functional details provided in the following description are non-limiting, but serve merely as a basis for the invention as defined by the claims provided herewith. The device described below can be modified as needed to conform to further development and improvement of materials without departing from the inventor's concept of the invention as claimed.

Figure 1A:
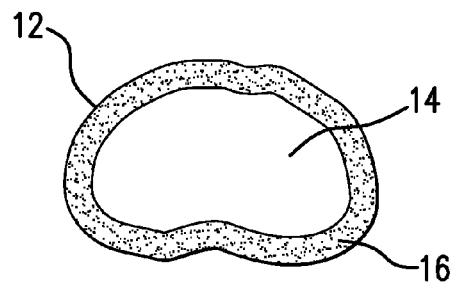
FIG. 1A shows an illustration of a cross section of an intervertebral disc having a normal anatomy.
Figure 1B:
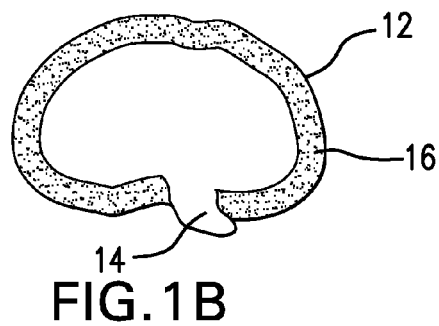
FIG. 1B shows an illustration of a cross section of a herniated intervertebral disc having a damaged annulus with protruding nucleus pulposus.
Figure 1C:
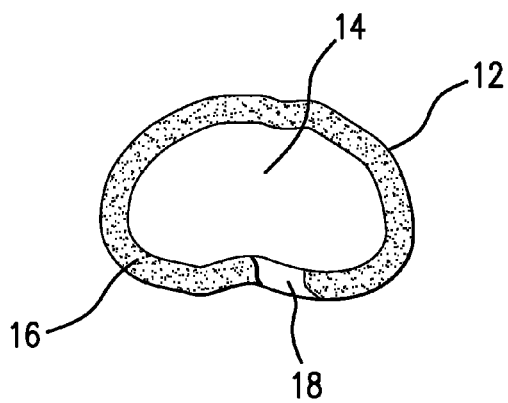
FIG. 1C shows an illustration of a herniated intervertebral disc after a partial disectomy for removal of extruded nucleus pulposus and damaged annulus fibrosis so as to create a rent or void in the disc annulus.
Figure 1D:
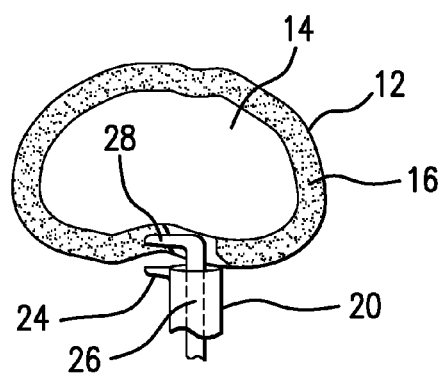
FIG. 1D shows an illustration of the use of instruments designed for use with the device of the present invention being employed to prepare the site in the annulus fibrosis for subsequent insertion of the device.
Figure 1E:
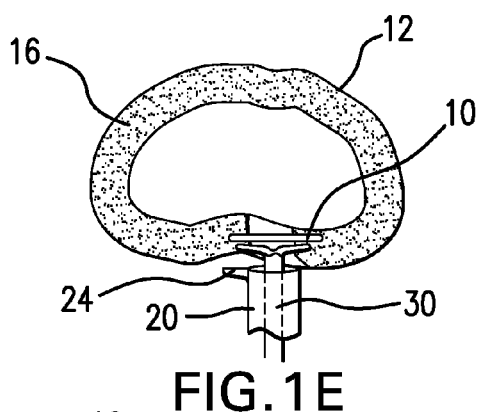
FIG. 1E shows an illustration of one embodiment of an insertion tool and the inserted device of the present invention in place in the annulus fibrosis of the herniated disc.

The device, as generally shown at 10 in FIGS. 1A-G, 5, 6, 7A-D, 8A-D, 9A-C, and 12A-D is a novel expandable device sized and configured to be easily inserted into a damaged portion of a herniated disc so as to occlude subsequent loss of nucleus pulposus from the repaired disc. As shown in FIG. 1A a normal intervertebral disc 12 primarily includes a centrally disposed nucleus pulposus 14 and a circumferentially disposed annulus fibrosis 16. When the annulus fibrosis 16 is damage, the nucleus pulposus 14 can be extruded through the damaged annulus 16 as shown in FIG. 1B. As discussed above, this condition of a herniated disc can be very painful and debilitating for a subject. As shown in FIG. 1C the method of the present invention normally requires that a partial disectomy be performed on the herniated disc for removal of extruded nucleus pulposus 14 and damaged portions of the annulus fibrosis 16 so as to create a void 18 in the disc annulus suitable for receiving an inserted device 10. Instruments specifically designed for use with the device 10 and method of the present invention can then be used to prepare the void 18 in the annulus fibrosis 16. As shown in FIG. 1D, FIG. 1E, and FIG. 2 a trocar device having at least one lumen 22 and an elongated foot 24 can be placed adjacent to the void 18 so as to control the direction and depth of penetration of other instruments inserted through the lumen 22 to the site of the void 18. As shown in FIG. 1D a device insertion site preparation tool 26 can be inserted through the lumen 22 to facilitate preparation of the annulus fibrosis 16. The preparation tool 26 can be provided with a curved and tapered end 27 having indicia 28 to aid in determining the depth of penetration of the penetration tool 26 into the annulus fibrosis 16. As shown in FIG. 1E, the device 10, can be implanted through the prepared area of the annulus fibrosis 16 using a device insertion tool 30, the exemplary embodiment of which is shown in FIG. 1E and FIGS. 12A-D.

Figure 1F:
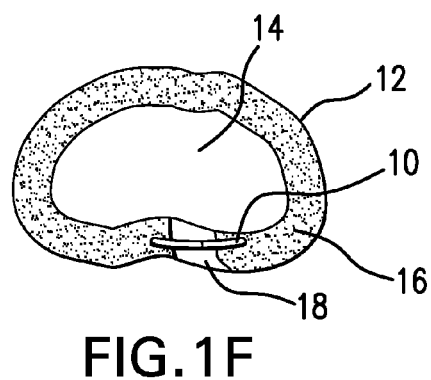
FIG. 1F shows an illustration of a cross section of a repaired herniated intervertebral disc with the device of the present invention fully inserted into the annulus fibrosis of the disc and the insertion tool shown in FIG. 1E removed.
Figure 1G:
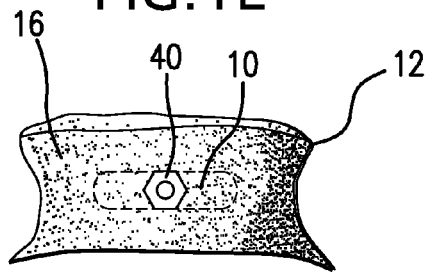
FIG. 1G shows an illustration of a side view of the repaired herniated intervertebral disc as shown in FIG. 1F.
Figure 1H:
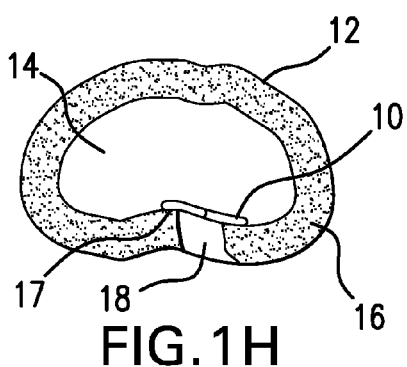
FIG. 1H shows an illustration of a side view of the repaired herniated intervertebral disc with the device of the present invention positioned within the nucleus pulposus adjacent to the inner surface of the annulus fibrosis.
Figure 7D:
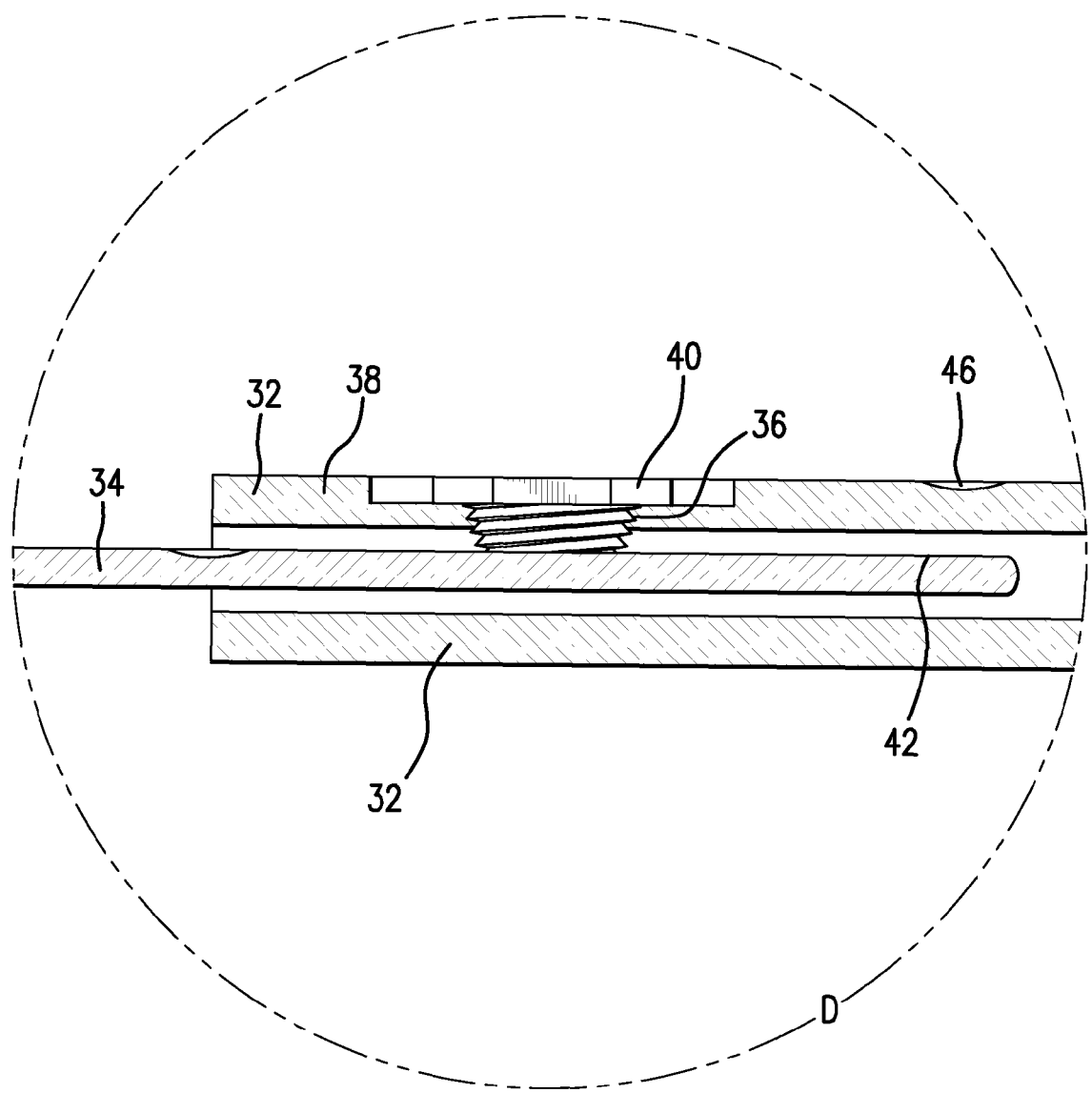
Figure 8D:
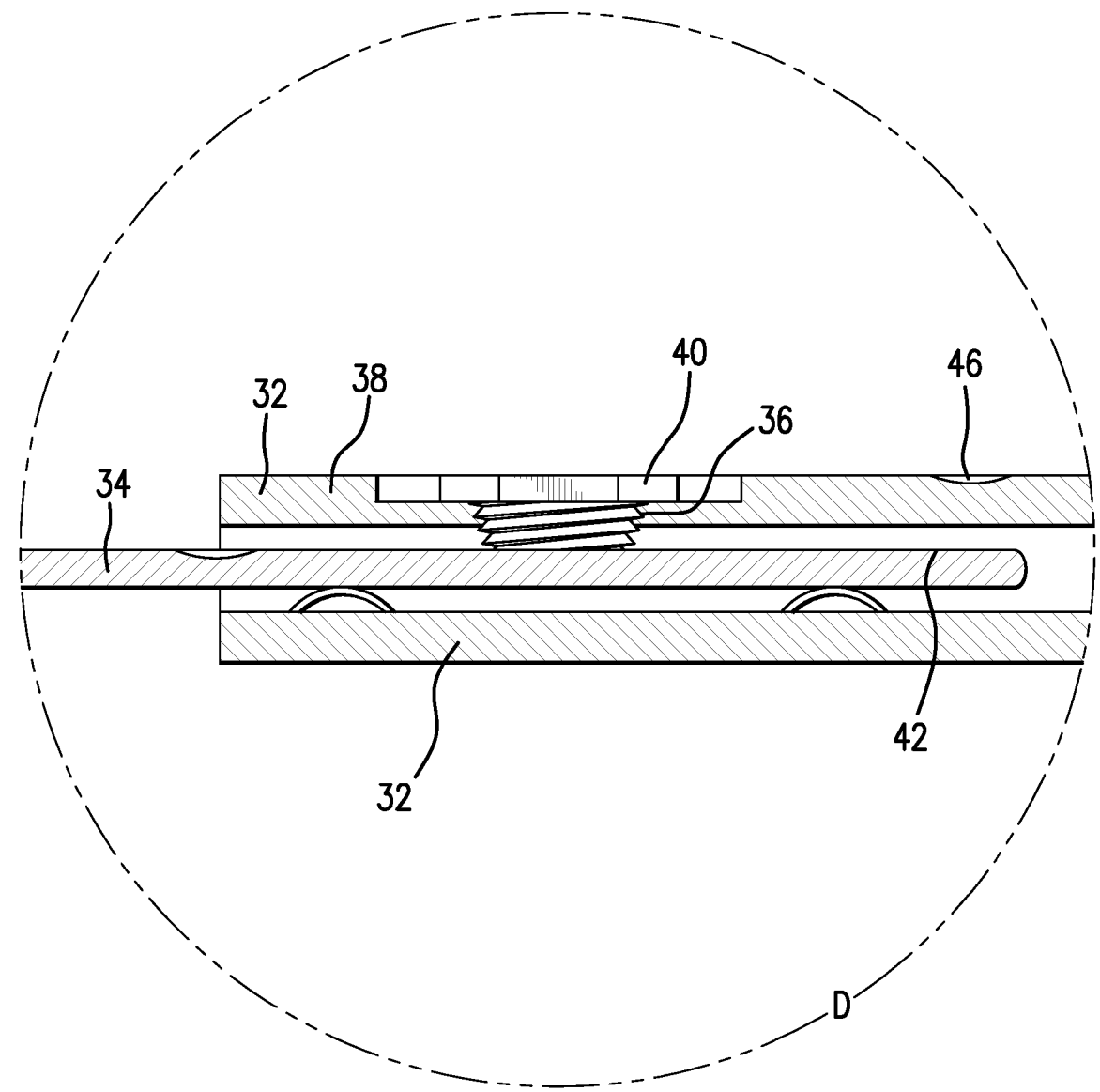

As shown in FIGS. 1F and 1G, the device 10, when fully inserted in the disc 12 occludes any subsequent loss of nucleus pulposus 14 from the now repaired herniated disc 12. The exemplary and preferred embodiment of the invention involves implanting the device 10 within the annulus fibrosis 16, as shown in FIGS. 1B-1G; however, it is within the concept of the invention, that the device 10 can be implanted in the nucleus pulposus immediately adjacent to the inner surface 17 of the annulus fibrosis 16 as shown in FIG. 1H.

As shown in FIGS. 1-E-G, FIGS. 5-6, FIGS. 7A-D, FIGS. 8-D, FIGS. 9-C the device 10 includes a first, elongated, exterior unit 32 and an extendable, second, elongated, interior unit 34 that is at least partially, slidably engaged and interiorly disposed within the first exterior unit 32. A locking element portal 36 is defined through the upper wall 38 of the first exterior unit 32. Threadably engaged with the locking element portal 36 is a locking element 40, which, when fully engaged in a locked position within the locking element portal 36, makes frictional contact with the upper surface 42 of the second interior unit 34. A length adjustment guide slot 44 is defined in the upper surface 42 of the second interior unit 34 and is sized and configured to slidably engage with the inwardly directed portion of the locking element 40 when the locking element 40 is in an unlocked position. Such slidable engagement serves to facilitate tracking of the second interior unit 34 when the length of the device 10 is selectively adjusted by a user. Also defined in the upper surface 38 of the second interior unit 34 and in the upper wall 38 of the first exterior unit 32 are multiple surface depressions 46. These surface depressions 46 provide gripping points on both the first exterior unit 32 and the second interior unit 34 for a device length adjusting tool 48. The length adjusting tool can be provided with a gripping handle 50, which can be shaped and/or provided with a textured surface 52 to facilitate use when being grasped by a user. The device length adjusting tool 48 can also be provided with a surface depression contact end 54, which facilitates manual sliding movement of the second interior unit 34 relative to the first exterior unit 32 when the length of the device 10 is selectively adjusted by a user. Other tools used with the device of the present invention can also be provided with a gripping handle 50 that can be shaped and/or textured to improve functionality.

As best shown in FIGS. 9A-C, the device 10 can be provided with at least one releasable anchoring element 56 attached to an anchoring activation member 62. The anchoring elements 56 are manufactured of a flexible yet resilient material and are preferably directed outwardly toward the side wall 58 of the first exterior unit 32. The anchoring elements 56 are sized so as to contact the inner surface of the side wall 58 and be bent downward when not deployed. The side wall 58 of the first exterior unit 32 defines a corresponding number of anchor portals 60 to the number of anchoring elements extending from the second interior unit 34. Due to resilient nature of the anchoring elements 56, as the anchoring member activation arm 62 is selectively slid longitudinally in relation to the first exterior unit 32, the anchoring elements 56 will eventually align with the anchor portals 60 of the first exterior unit side wall 58 and deploy their terminal portions 64. The anchoring member activation arm 62 extends into both the first exterior unit 32 and the second interior unit 34 and is connected in the middle by an anchor activation cam mechanism 66, which can be manually selected by insertion of any tool capable of applying torque to the cam mechanism 66. Upon activation of the cam mechanism 66, the locking element 40 can be inserted and tightened to hold the cam mechanism 66 and the underlying second interior unit 34 in the selected position. The unlocked cam mechanism 66 is capable upon being rotated of moving the anchoring activation arm 62 from an anchor stowed position to an anchor activated position and upon reversal of the rotational movement of the cam mechanism 66 to move the anchor activation arm 62 from an anchor activated position to an anchor stowed position. FIGS. 9A and 9B show the device in an anchor activated position while FIG. 9C shows the device in an anchor stowed position. While the above described exemplary embodiment and the method of implanting the device in the annulus fibrosis as shown in FIGS. 1D-G is preferred, it is within the scope of the present invention, as shown in FIG. 1H to implant the device 10 in the nucleus pulposus of the disc at a position adjacent to the inner surface 17 of the annulus fibrosis 16 and when so implanted, the device 10 can be modified such that the anchor portals 60 are positioned to direct the anchoring elements 56 out of the top or bottom of the device 10.

Figure 10:
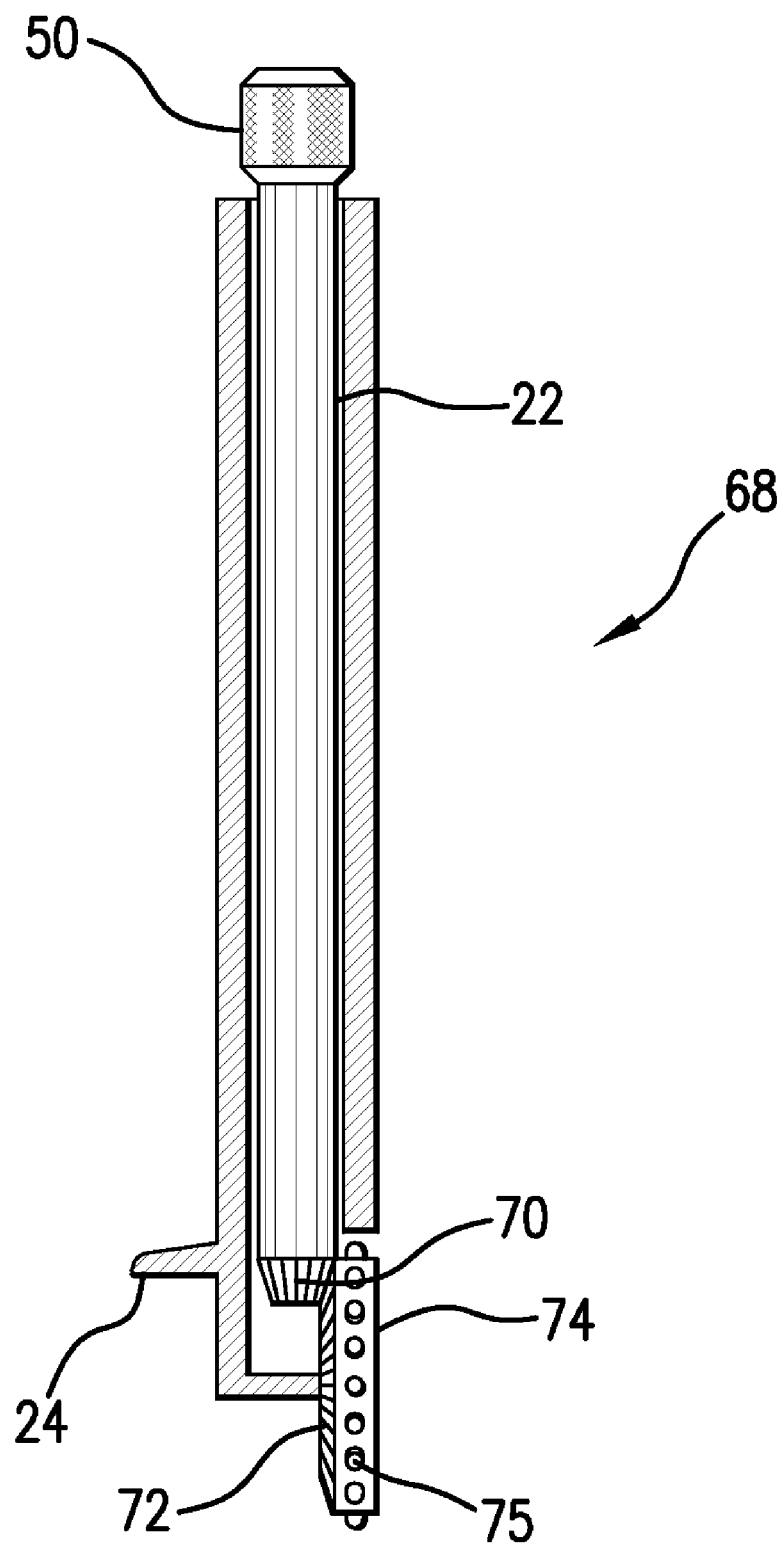
FIG. 10 shows an illustration of a length adjustment instrument for use with the device of the present invention, the length adjustment instrument having surface depression contact protrusions configured to contact surface depressions on the surface of the device of the present invention so as to selectively lengthen or shorten the size of the device by moving the two slidably connected portions of the device relative one to the other.

As shown in FIG. 10, another embodiment of a length adjustment tool, generally shown at 68, can be configured employing a hypoid gear 70 that drives a geared running wheel 72 having a connected cog wheel 74. As the handle 50 is turned by a user, the shaft 76 transmit the torque to the hypoid gear 70 that, by its operational connection to the geared running wheel 72, changes the direction of rotation of the shaft 76 through a 90 degree angle. By changing the angle of rotation, the a connected cog wheel 74 is rotated so as to bring each of the protruding cogs 75 into contact with the surface depressions 46 on the upper surface of the second interior unit 34 thus slidably moving it from within its position in the first exterior unit 32. Reversal of the torque applied to the handle 50 can reverse the operation and thus stow the second interior unit 34 back inside the first exterior unit 32 when it is desired to reposition or to remove the device from the annulus fibrosis of the disc. As with the trocar 20, the alternative length adjustment tool 68 is provided with a lumen 22 and can be provided with an elongated foot 24 to assist in proper positioning of the tool 68.

Figure 11:
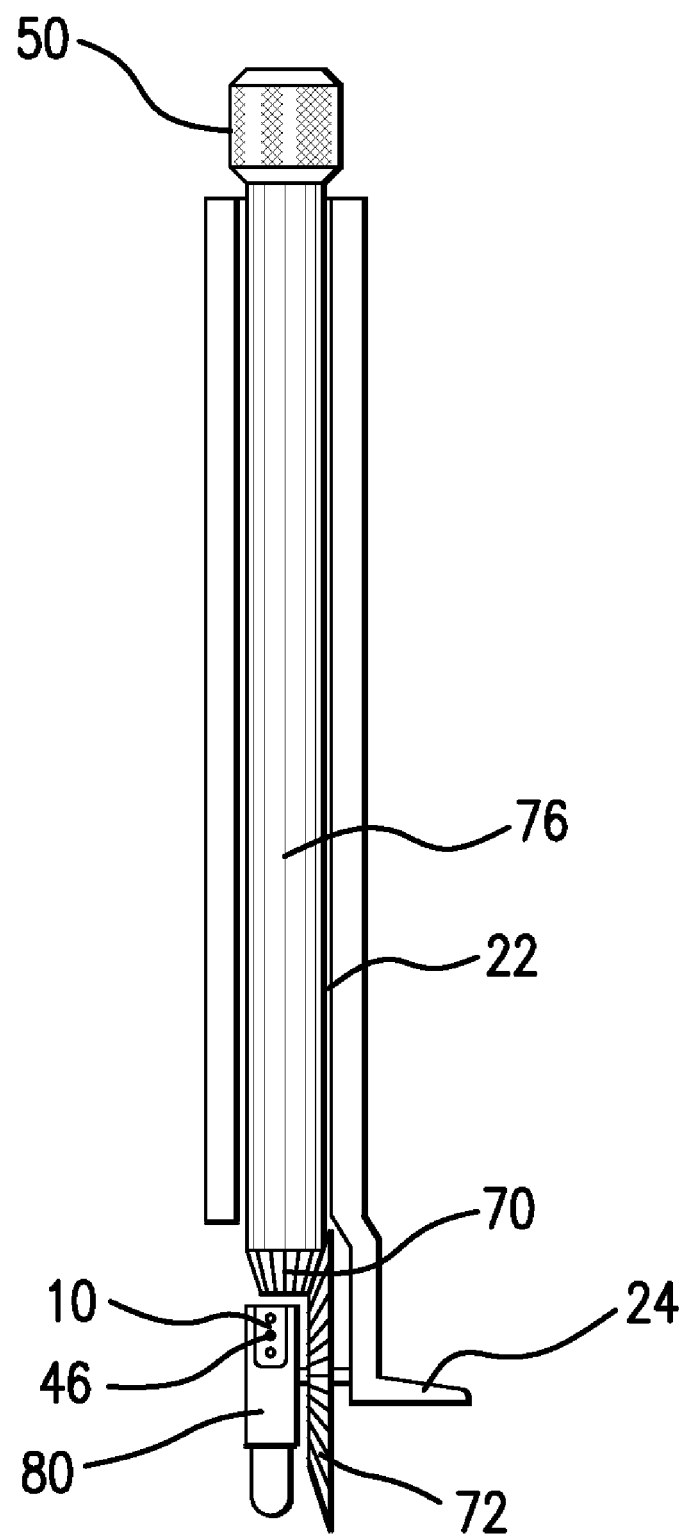
FIG. 11 shows an illustration of a tool configured to facilitate insertion of the device of the present invention into the annulus fibrosis of a herniated intervertebral disc. Shown with the tool is an embodiment of the device of the present invention in a partially deployed configuration on the insertion wheel of the tool.

As best shown in FIG. 11, an alternative device insertion tool 78 can be provided using a similar hyphoid gear 70 mechanism working with a geared running wheel 72 to change the direction of rotation of the shaft 76 through a 90 degree angle. For this alternative device insertion tool 78 changing the direction of rotation enables a device deployment wheel 80 to rotate and in doing so to deploy the device 10 from its stored position on the deployment wheel 80 into the annulus fibrosis 16 of the disc 12. As with the trocar 20 and the alternative length adjustment tool 68 described above, the alternative device insertion tool 78 is provided with a lumen 22 and can be provided with an elongated foot 24 to assist in proper positioning of the tool 78.

Figure 12A:
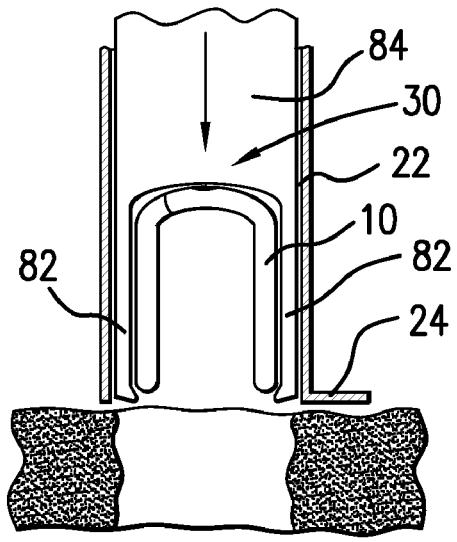
FIGS. 12A-D show an alternative embodiment of a device insertion tool in FIG. 12A the device positioned within a trocar ready for insertion downward into the hole in the disc annulus, in FIG. 12B the device in a partially extended configuration within and moving downward into the disc annulus, in FIG. 12C the device fully inserted and extended in the annulus fibrosis as the insertion tool is retracted from the disc annulus, and in FIG. 12D the device fully inserted and extended within the disc annulus and the insertion tool fully retracted from the disc annulus and back into the trocar.
Figure 12B:
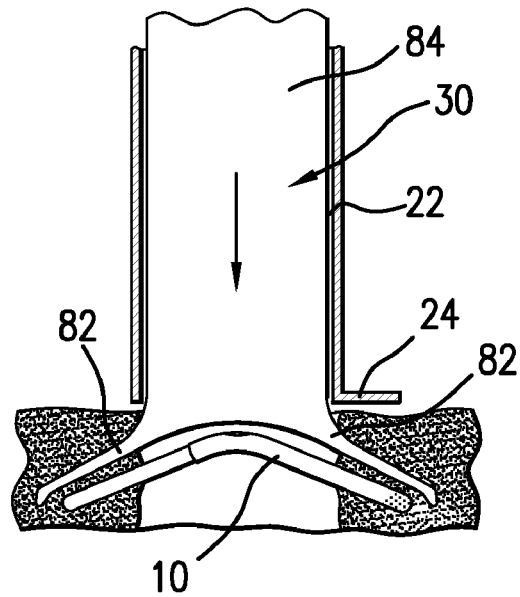
Figure 12C:
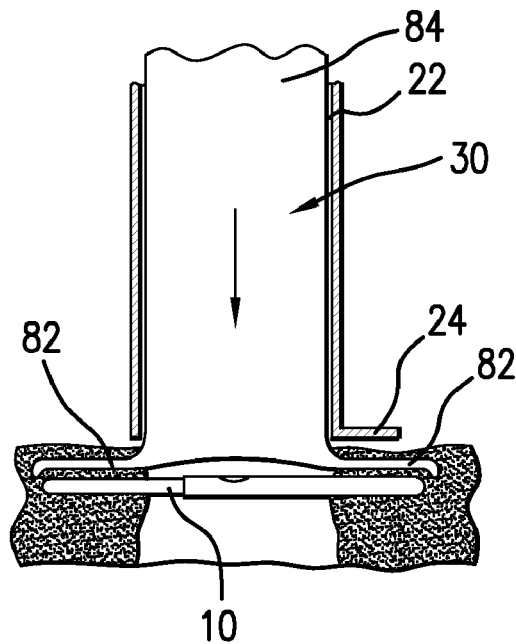
Figure 12D:
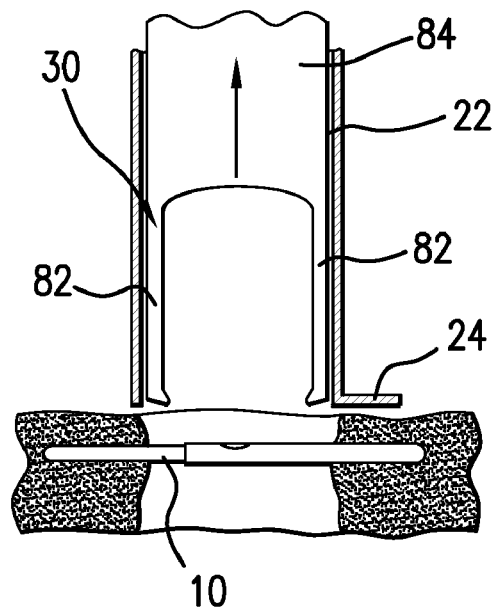

The embodiment of the device insertion tool 30 shown for illustration in FIG. 1E is shown in greater detail in FIGS. 12A-D. As shown in this progression of figures, the insertion tool 30 includes a slidable shaft 84 sized to pass within the lumen 22 of the trocar 20 and terminating in two opposing arms 82. When compacted within the lumen 22 of the trocar 20, the opposing arms 82 of the insertion tool 30 securely hold the device 10 in a flexed or folded configuration. When moved downward through the lumen 22 and outward from the lumen 22, the opposing arms 82, which are outwardly biased are permitted to spread gradually, thus deploying the device 10 and simultaneously inserting it into the annulus fibrosis 16 of the disc. This embodiment of an insertion tool 30 is provided as a simple exemplary disclosure; however, it is a non-limiting example and variations of insertion tools are limited only by the claims and are within the concept of the present invention. In the above example, the device 10 can be that as described above having a first elongated exterior unit 32 and a second elongated interior unit 34, which are slidably engaged with each other thus permitting the device 10, when unfolded as shown in FIG. 12C to be adjustable in length and capable of being anchored in place. It is also within the concept of the present invention that the device 10 can be modified such that the extension ability of the device is limited to the unfolding of the device as shown in FIGS. 12B and 12C. Similarly, anchoring features of the device 10, as described above and shown in an exemplary embodiment in FIGS. 9A-C may or may not be included in the device 10 when positioned using the insertion tool 30 demonstrated in FIGS. 12A-D.

The features of the device 10 can be embodied in various configurations and combinations, not all of which have been recited in the examples discussed herein. The components of the device 10 can be manufactured in various sizes of varying relative dimensions, cross-sectional geometry and varying radii of curvature to conform to the natural shape of the annulus fibrosis of the disc. Furthermore, it is also within the understanding of the inventors that the device can be manufactured of any known materials having the necessary strength and resiliency to meet the operational requirements of the invention. Such variations in the device 10 can be used as necessary to improve the function of the device for the needs of a particular patient.

The device 10 can be manufactured as components by methods known in the art, to include, for example, molding, casting, forming or extruding, and machining processes. The components can be manufactured having a variety of different dimensions so as to provide components that can be selected by the surgeon as being best suited to the anatomical size and conformation of individual patient's disc in need of repair. Non-limiting examples of materials that may be used at least in part for components of the device 10 include, for example, implant grade metallic materials, such as titanium, titanium alloy, cobalt-chromium alloys, stainless steel, and the like. Additionally, the structures of the device 10 can be manufactured wholly or in part using non-metallic materials such as, for example, ceramic, PEEK, PEKK, or other suitable non-metallic materials. It is also within the concept of the invention that the device 10 can be made of bioresorbable materials.

The device 10 can be implanted using a posterior or transforaminal-posterior approach whereby the device 10 can be inserted through an open incision or through a minimally invasive incision. The instruments described herein that can be employed to implant the device 10 or to adjust the length of the device 10 are non-limiting examples and other instruments found to be suitable for the function can also be used without departing from the concept of the invention of the device and method.

It is also within the concept of the present invention to provide a kit, which includes the at least one of the devices 10, which can be provided in various sizes, as well as tools to facilitate the surgical procedure and additional instruments and/or implants or components which can be employed as deemed necessary by the surgeon/user. Such a kit can be provided with sterile packaging to facilitate opening and immediate use in an operating room.

Each of the embodiments described above are provided for illustrative purposes only and it is within the concept of the present invention to include modifications and varying configurations without departing from the scope of the invention that is limited only by the claims included herewith.

What is claimed is:

1. An implantable device for repairing a damaged intervertebral disc in a subject, the device comprising
   an elongated extendable device comprising a first elongated exterior unit and a second elongated interior unit, at least a portion of said second elongated interior unit being slidably engaged and interiorly disposed with said first elongated unit, said second elongated interior unit being extendable from a closed to an extended position relative to said first elongated exterior unit;
   a locking element threadably engaged with a locking element portal defined in the upper surface of said first elongated exterior unit, said locking element being capable of contacting said interiorly disposed second interior unit when said elongated interior unit has been slidably extended from a closed position to an extended position relative to said first elongated unit and said locking element is moved into a locked position;
   a centrally disposed anchoring activation member engaged with multiple anchoring elements connected to said second elongated interior unit, said activation member when selectively moved can cause coordinated movement of said multiple anchoring elements from a closed position to an anchored position; and
   multiple anchoring portals defined in at least one exterior wall of said first elongated exterior unit, said anchoring portals having a complementary number to the number of anchoring elements, said anchoring portals being sized and configured to permit bidirectional movement of said anchoring elements through said anchoring portals in response to movement of said anchoring activation member.

2. The device of claim 1, further comprising an anchor activation cam mechanism rotationally mounted in said device, said cam mechanism being capable upon being rotated of moving said anchoring activation member from an anchor activated position to an anchor stowed position.

3. An implantable device in combination with an insertion system, the combination comprising:
   an implantable device comprising:
   an elongated extendable device comprising a first elongated exterior unit and a second elongated interior unit, at least a portion of said elongated interior unit being slidably engaged and interiorly disposed within said first elongated exterior unit, said second elongated interior unit being extendable from a closed to an extended position relative to said first elongated exterior unit;
   a locking element threadably engaged with a locking element portal defined in the upper surface of said first elongated exterior unit, said locking element being capable of contacting said interiorly disposed second interior unit when said second elongated interior unit has been slidably extended from a closed position to an extended position relative to said first elongated exterior unit and said locking element is moved into a locked position,
   wherein said elongated implantable device is sized and configured to be implantable through a void in the annulus fibrosis of a vertebral disc and selectively extended with the disc so as to occlude leakage of material from the void; and
   an insertion system, comprising:
   an insertion trocar, said insertion trocar comprising an elongated trocar having a through lumen and at a distal end terminating in an elongated food, said foot being sized and configured to facilitating positioning of said trocar adjacent to a void in a site of a vertebral disc annulus fibrosis in need of repair, said trocar lumen being sized to permit passage and manipulation of elongated tools into the site in need of repair;

an elongated site preparation tool having a distal tapered end displaying length indicia for facilitating preparation of the annulus fibrosis to receive the device of the present invention;

a device insertion tool, said insertion tool being configured to releasably hold said device of claim 1 and insert said device into position with a void in the annulus fibrosis of a damaged vertebral disc and selectively release said device into the annulus fibrosis;

a length adjustment tool having a distal end configured complementary to the shape of said surface depressions of said device and to be capable of selectively manipulating said second elongated interior unit of said device relative to said first elongated exterior unit of said device from a closed position to an extended position relative to said first elongated exterior unit or from an extended position to a closed position.

4. The combination of claim 3, wherein said insertion tool comprises an elongated tubular body with an internally disposed and rotatable drive shaft, said drive shaft terminating in a hypoid gear mechanism engaged with a geared running wheel, wherein directional rotation of said drive shaft is redirected substantially 90 degrees, said geared running wheel being capable of holding said device until rotation of said running wheel deploys said device into a void in the annulus fibrosis of a damaged vertebral disc.

5. The combination of claim 3, wherein said insertion tool comprises an elongated tubular body having a lumen, said lumen containing an internally slidable insertion shaft, said insertion shaft terminating in opposing arms, said opposing arms when compacted with said lumen holding said device of the combination in a flexed configuration, said opposing arms being biased outward and being capable of spreading apart and releasing said device when said slidable insertion shaft drives said opposing arms and said held device outside of said lumen and into a void in the annulus fibrosis of a damaged vertebral disc.

6. The combination of claim 3, wherein said length adjustment tool comprises an elongated tubular body having a lumen said lumen containing an internally rotatable shaft, said rotatable shaft terminating in a hypoid gear that drives a geared running wheel having a connected cog wheel with multiple protruding cogs corresponding in size and position so as to be complementary to the surface depressions on the upper surface of said second elongated interior unit of the device of said combination, wherein rotational movement of said rotatable shaft is translated substantially 90 degrees so as to make said length adjustment tool capable of bringing each of said protruding cogs into contact with the surface depressions on the upper surface of the second elongated interior unit and being capable of driving said second elongated interior unit outward from its internally disposed position with said first elongated unit.

* * * * *